United States Patent
Danziger et al.

(10) Patent No.: US 11,730,101 B1
(45) Date of Patent: Aug. 22, 2023

(54) *RUMEX* PLANT NAMED 'DRUMFOHNID'

(71) Applicant: Danziger DAN' Flower Farm, Beit Dagan (IL)

(72) Inventors: Gavriel Danziger, Beit Dagan (IL); Amir Zuker, Beit Dagan (IL); Noam Shpayer, Beit Dagan (IL)

(73) Assignee: Danziger "DAN" Flower Farm

( * ) Notice: Subject to any disclaimer, the term of this patent is extended or adjusted under 35 U.S.C. 154(b) by 0 days.

(21) Appl. No.: 17/871,910

(22) Filed: Jul. 23, 2022

(51) Int. Cl.
*A01H 5/12* (2018.01)
*A01H 6/00* (2018.01)

(52) U.S. Cl.
CPC ................. *A01H 6/00* (2018.05); *A01H 5/12* (2013.01)

(58) Field of Classification Search
CPC ..................................... A01H 5/12; A01H 6/00
See application file for complete search history.

*Primary Examiner* — Susan McCormick Ewoldt
(74) *Attorney, Agent, or Firm* — Cassandra Bright

(57) ABSTRACT

The invention relates to the field of *Rumex crispus*, specifically, the variety designated 'DRUMFOHNID'. The variety 'DRUMFOHNID' is characterized by tall flowering stems with green tepals, sepals and fruits arranged in an asymmetrical pattern along the stem. The new variety begins flowering early and produces a small foliar rosette.

9 Claims, 4 Drawing Sheets
(4 of 4 Drawing Sheet(s) Filed in Color)

RUMEX PLANT NAMED 'DRUMFOHNID'

Latin name of the genus and species: *Rumex crispus*.
Variety denomination: 'DRUMFOHNID'.

FIELD OF THE INVENTION

The present invention relates to a new, distinct and stable variety of *Rumex crispus*, hereinafter referred to as 'DRUMFOHNID'. The present invention relates to seeds which are the *Rumex crispus* 'DRUMFOHNID', as well as plants and plant parts produced by these seeds which have all of the morphological and physiological characteristics of the *Rumex crispus* 'DRUMFOHNID'. The present invention also relates to methods for producing these seeds and plants of the *Rumex crispus* 'DRUMFOHNID'. Furthermore, the present invention relates to a method of producing progeny *Rumex* plants by crossing *Rumex* 'DRUMFOHNID', as either the seed or pollen parent, with another *Rumex* plant and selecting progeny.

BACKGROUND OF THE INVENTION

The present invention relates to a new, distinct and stable variety of *Rumex crispus*, and hereinafter referred to by the variety denomination 'DRUMFOHNID'. The new *Rumex* 'DRUMFOHNID' originated from a crossing made in a controlled breeding program by the inventors in July of 2014, and selected in December of 2015, in Mishmar Hashiva, Israel. The parent is the *Rumex crispus* proprietary line identified by code 'RUM-16-6' (unpatented). This proprietary line is the sole parent, as the new variety 'DRUMFOHNID' is the result of a self—crossing of this individual parent variety.

The new variety was selected from the F7 generation. The F1 generation was created by open-pollination, the subsequent generations by single seed descent. The F1 'RUM-16-6' parent variety was observed to have approximately 47% homozygosity for the desired traits which were stabilized in the subsequent 6 generations. All parentage beginning with the F1 generation is unavailable to the public and unpatented. The breeding scheme can be found in FIG. 4

*Rumex* is a member of the Polgonaceae family, known in layman's terms as "the buckwheat family". *Rumex crispus* is a vascular land plant, native to Europe and Western Asia. *Rumex* has been widely spread throughout many parts of the world by human activity. *Rumex crispus* plants are perennial and can thrive in a variety of settings, including standing water. It is widely found in areas disturbed by humans.

*Rumex crispus* have not been developed for commercial ornamental purposes. The inventors are unaware of other commercial or hobbyist breeding programs to develop this Genus.

Plants of *Rumex* form a broad leaf basal rosette and produce study flower stalks which are a panicle of racemes. Individual flowers are composed of sepals and outer tepals, with no true petals present.

Theoretically, asexual propagation of *Rumex* can be performed by plant division, however, propagation is exclusively performed by sexual means, by seed.

The *Rumex crispus* seeds and plants produced by this method are uniform with respect their morphological and physiological characteristics.

Methods for cultivation and crossing of *Rumex* are not well known. Amateur seed suppliers advertise *Rumex crispus* under the "Curly Dock".

A basic reference to the species can be found in: "*Rumex crispus*". Flora of North America: Magnoliophyta: Caryophyllidae, pt. 2. Oxford University Press. 2005. which is herein incorporated by reference. This reference gives a basic botanical description of *Rumex crispus*.

Due to its successful adaptation to a variety of environmental conditions, new varieties of *Rumex crispus* cultivars with improved commercial features can be a valuable asset to the commercial grower. The new *Rumex* 'DRUMFOHNID' was developed through a controlled breeding program and exhibits unique, desirable and stable characteristics.

The breeders have produced a new variety of *Rumex crispus*, as an ornamental plant useful for cut flower production. Whilst reducing the present invention to practice, the present inventors were able, to generate a unique variety of *Rumex crispus*.

SUMMARY OF THE INVENTION

The present invention provides *Rumex* plant selections that produce tall flowering stems with green tepals, sepals and fruits arranged in an asymmetrical pattern along the stem. Additionally, the new variety begins flowering early and produces a small foliar rosette. These qualities distinguish the new cultivar from typical *Rumex crispus* plants found in the wild.

These and other objectives have been achieved in accordance with the present invention which provides 'DRUMFOHNID' as a new *Rumex* cultivar that is a product of a planned breeding program conducted by the inventors. The parent is the *Rumex crispus* inbred line identified by code 'RUM-16-6' (unpatented).

The parental cultivar has a sufficient degree of homozygosity such that the progeny of the cross are genetypically and phenotypically uniform. The new *Rumex crispus* 'DRUMFOHNID' therefore can be produced by sexual reproduction by crossing the parent inbred line identified by the code 'RUM-16-6' to produce a population of progeny plants, each of which has the combination of characteristics as herein disclosed for the new *Rumex crispus* 'DRUMFOHNID'.

Seeds which are variety 'DRUMFOHNID' are produced by crossing the parental inbred line identified by the code 'RUM-16-6' and having been deposited May 19, 2022 with the National Collection of Industrial Food and Marine Bacteria(NCIMB), Ferguson Building, Bucksburn, Aberdeen, Scotland AB21 7GB and assigned Deposit Accession number NCIMB 43987. The NCIMB is a Budapest Treaty recognized depository which affords permanence of the deposit.

OBJECTS OF THE INVENTION

The following embodiments and aspects thereof are described in conjunction with system, tools and methods which are meant to be exemplary, not limiting in scope.

The present invention, in some embodiments thereof, relates to *Rumex crispus* plants as well as parts and uses of these plants.

The present invention provides *Rumex* plant selections with tall flowering stems with green tepals, sepals and fruits arranged in an asymmetrical pattern along the stem. Flowering of the new variety begins early and the foliar rosette is small. These characteristics in combination distinguish the new cultivar from typical *Rumex crispus* varieties.

These and other objectives have been achieved in accordance with the present invention which are the product of a planned breeding program conducted by the inventors. One embodiment of this invention is the *Rumex* variety 'DRUMFOHNID' described herein.

Seeds which can be used to produce the variety 'DRUMFOHNID' which have been deposited May 19, 2022 with the National Collection of Industrial Food and Marine Bacteria (NCIMB), Ferguson Building, Bucksburn, Aberdeen, Scotland and assigned accession number 43987. The NCIMB is a Budapest Treaty recognized depository which affords permanence of the deposit.

Another embodiment relates to a plant produced from seeds which are *Rumex crispus* 'DRUMFOHNID'.

Another embodiment relates to a plant produced by vegetative means which are *Rumex crispus* 'DRUMFOHNID'. The present invention also relates to plant parts, such as pollen, seeds or inflorescences and individual flowers produced by *Rumex crispus* 'DRUMFOHNID'.

Another embodiment relates to a method of producing seed which are *Rumex crispus* 'DRUMFOHNID'.

Another embodiment also relates to a method of producing plants having all the physiological and morphological characteristics of the *Rumex crispus* 'DRUMFOHNID'. comprising the steps of (a) self-pollinating *Rumex crispus* 'DRUMFOHNID'. (b) harvesting seeds produced from said cross; and (c) producing plants from said harvested seeds.

The present invention also relates to producing progeny plants from the cross of *Rumex crispus* 'DRUMFOHNID', as the female or male parent, with another *Rumex* or other plant, and selecting progeny plants from this cross.

The present invention also relates to producing progeny plants of *Rumex crispus* 'DRUMFOHNID', by any means of vegetative propagation.

The present invention also relates to producing progeny plants of *Rumex crispus* 'DRUMFOHNID', from natural or induced mutation.

Another embodiment relates to tissue culture produced from protoplast of cells from the *Rumex* plant disclosed in the subject application, wherein said cells or protoplasts are produced from a plant part selected from the group consisting of pollen, ovules, embryos, protoplasts, meristematic cells, callus, leaves, anthers, cotyledons, hypcotyl, pistils, roots, root tips, flowers, seeds, petiole and stems.

Another embodiment relates to a plant or a part thereof, produced by growing *Rumex crispus* 'DRUMFOHNID', wherein the plant part comprises at least one cell of *Rumex crispus* 'DRUMFOHNID'.

Another embodiment relates to tissue or cell culture of regenerable cells produced from the plants of *Rumex crispus* 'DRUMFOHNID'. This includes a *Rumex crispus* plant regenerated from the tissue or cell culture of *Rumex crispus* 'DRUMFOHNID'.

Another embodiment relates to a method of vegetatively propagating the plant *Rumex crispus* 'DRUMFOHNID' comprising the steps of: collecting tissue or cells capable of being propagated from a plant of *Rumex crispus* 'DRUMFOHNID'; cultivating said tissue or cells to obtain proliferated shoots; and rooted said shoots to obtain rooted plantlets; or cultivating said tissue or cells to obtain shoots or to obtain plantlets and a plant produced by growing the plantlets or shoots of said plant.

A further embodiment relates to a method for developing a *Rumex crispus* plant in a *Rumex* breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the *Rumex* plant of *Rumex crispus* 'DRUMFOHNID', or its parts, wherein application of said techniques results in development of an *Rumex crispus* plant.

A further embodiment relates to a method of introducing a mutation into the genome of *Rumex crispus* 'DRUMFOHNID', and wherein the resulting plant comprises at least one genome mutation and producing plants therefrom.

In addition to the exemplary aspects and embodiments described above, further aspects and embodiments will become apparent by study of the following descriptions.

The cultivar 'DRUMFOHNID' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DRUMFOHNID' These characteristics in combination distinguish 'DRUMFOHNID' as a new and distinct *Rumex* cultivar:

1. Tall flowering stems.
2. Green tepals, sepals and fruits arranged in an asymmetrical pattern along the stem.
3. Early flowering.
4. Small foliage.

PARENT COMPARISON

Plants of the new cultivar 'DRUMFOHNID' are similar to plants of the parent in most horticultural characteristics, however, plants of the new cultivar 'DRUMFOHNID' differ in the following;

1. Plants of the new variety begin flowering earlier than plants of the parent variety.
2. Plants of the new variety have smaller foliage than the parent variety.

WILD TYPE COMPARISON

Plants of the new cultivar 'DRUMFOHNID' can be compared to the wild type *Rumex crispus* widely found in disturbed landscapes. These plants are similar in most horticultural characteristics;

1. Plants of the new variety flower earlier than plants of the wild type.
2. Plants of the new variety produce less foliage than plants of the wild type.
3. Foliage of the new variety is smaller than foliage of the wild type.

BRIEF DESCRIPTION OF THE FIGURES

The patent or application file contains at least one drawing executed in color. Copies of this patent or patent application publication with color drawings will be provided by the Office upon request and payment of the necessary fees.

The accompanying photographs illustrate the overall appearance of the new *Rumex crispus* 'DRUMFOHNID' showing the colors as true as is reasonably possible with colored reproductions of this type. Colors in the photographs may differ slightly from the color values cited in the detailed botanical description which accurately describes the color of 'DRUMFOHNID'.

DETAILED BOTANICAL DESCRIPTION

Figure 1:
FIG. 1 shows a side view perspective of a typical flowering plant of 'DRUMFOHNID', at approximately 11 weeks old.
Figure 2:
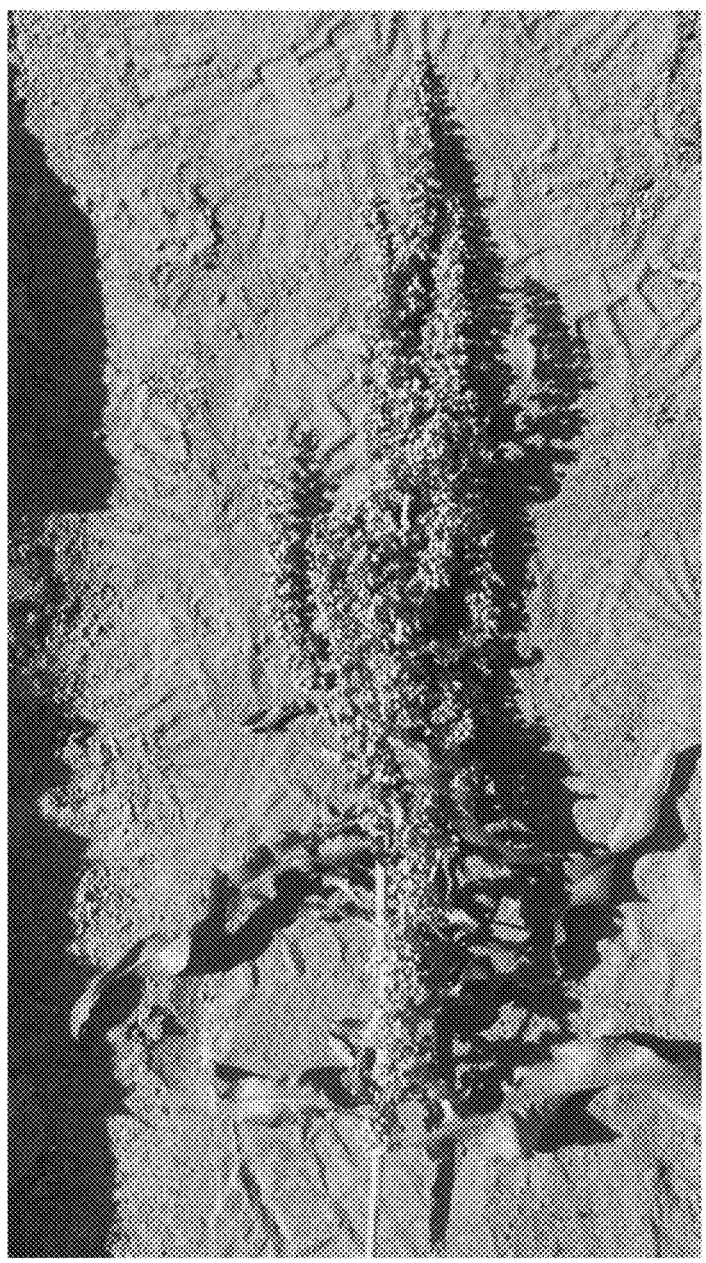
FIG. 2 shows a side view perspective of typical inflorescences of 'DRUMFOHNID'.
Figure 3:
FIG. 3 illustrates a closer view of the flowers.
Figure 4:
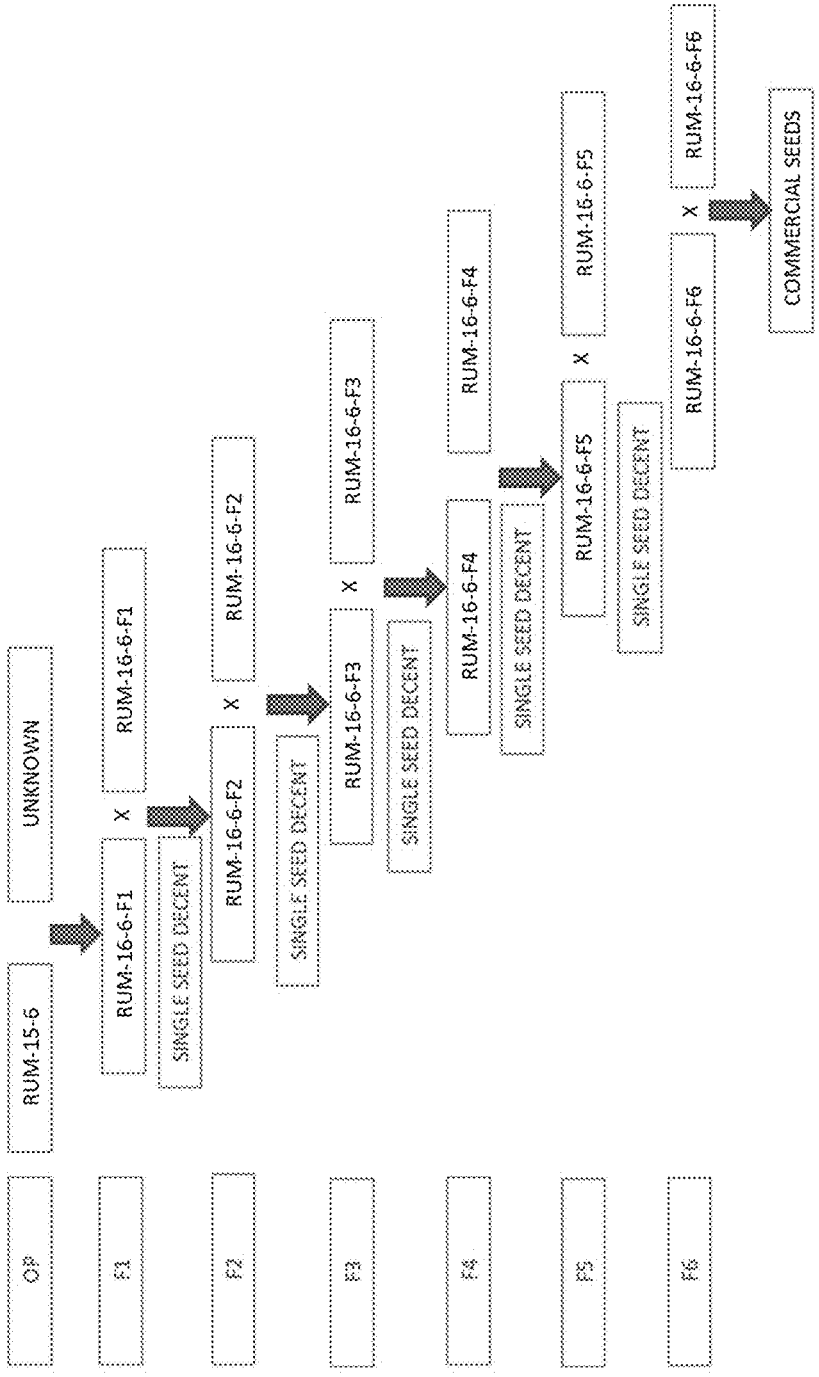
FIG. 4 describes the breeding scheme used to develop 'DUMFOHNID'.

This invention is directed to *Rumex* plant having all the morphological and physiological characteristics of the variety 'DRUMFOHNID' produced from seeds which are the product of the self-cross of the *Rumex crispus* inbred line identified by code 'RUM-16-6' (unpatented). The parent has a sufficient degree of homozygosity such that the progeny of the cross were, and continue to be, phenotypically uniform. The new variety 'DRUMFOHNID' can therefore be produced by sexual reproduction by crossing of the inbred selection identified by the code 'RUM-16-6' to produce a population of progeny plants, each of which has the combination of characteristics herein disclosed for the new variety 'DRUMFOHNID'.

'DRUMFOHNID' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, and size of inflorescences can result depending on the growing conditions. Typically, these plants are produced outdoors, and variations in temperature and humidity can produce different results.

The aforementioned photographs, together with the following observations, measurements and values describe the new *Rumex* 'DRUMFOHNID' as grown in a greenhouse in Mishmar Hashiva, Israel, during Winter to Spring. Plants of 'DRUMFOHNID' were grown with day temperatures ranging from about 20° C. to 30° C. and night temperatures ranging from about 8° C. to 15° C. No chemical or light treatments were given. Day length was approximately 9 to 13 hours, throughout the growing period.

Color references are made to The Royal Horticultural Society Colour Chart (R.H.S.), 2005 mini edition, except where general colors of ordinary significance are used. Color values were taken under daylight conditions in a greenhouse Mishmar Hashiva, Israel. The age of the plants of 'DRUMFOHNID' described is about 14 weeks from planting a rooted cutting.

Botanical classification: *Rumex crispus*.
Parentage:
　　*Parent.*—*Rumex crispus* inbred line identified by code 'RUM-16-6' (unpatented).

PROPAGATION

Time for produce a rooted liner: Approximately 4 weeks from sowing seed to a viable young plant for transplant.

PLANT

Growth habit: Erect.
Height: Approximately 150 cm to 250 cm.
Plant spread: Approximately 80 cm.
Growth rate: Approximately 14 weeks to a mature plant from a young plant.
Branching characteristics: Branches along the main stem.
Length of primary lateral branches: Approximately 85 cm.
Diameter of lateral branches: Approximately 0.5 cm.
Quantity of primary lateral branches: Approximately 6 lateral branches.
Characteristics of primary lateral branches: Without lateral branches.
　　*Form.*—Round.
　　*Color.*—Near RHS Yellow-Green 147C.
　　*Texture.*—Glabrous.
　　*Strength.*—Strong.
Internode length: Varies along the stem. Approximately 22 cm for the lower part of the stem, approximately 6 cm for the middle part and approximately 2 mm for the upper part of the stem.

FOLIAGE

Leaf:
　　*Arrangement.*—Rosette.
　　*Quantity.*—Average 15.
　　*Average length.*—Approximately 40 cm.
　　*Average width.*—Approximately 12 cm.
　　*Shape of blade.*—Elliptic.
　　*Apex.*—Acute.
　　*Base.*—Attenuate.
　　*Margin.*—Entire.
　　*Texture of top surface.*—Glabrous.
　　*Texture of bottom surface.*—Glabrous.
　　*Appearance, top surface.*—Matte.
　　*Appearance, bottom surface.*—Matte.
　　*Aspect.*—Wavy.
　　*Color.*—Young foliage upper side: Near RHS Green 137C. Young foliage under side: Near RHS Yellow-Green Green 146B. Mature foliage upper side: Near RHS Green 137B. Mature foliage under side: Near RHS Yellow-Green 147B.
　　*Venation.*—Type: Parallel. Venation color upper side: Near RHS Green 137D. Venation color under side: Near RHS Yellow-Green 147B.
　　*Petiole.*—Length: Average of 14 cm for mature foliage. Diameter: Approximately 0.5 cm for mature foliage. Color: Approximately RHS Yellow-Green 146D for mature foliage. Texture: Smooth.

FLOWER

Natural flowering season: Spring and summer (February to August in Israel).
Days to flowering from rooted cutting: Approximately 10-14 weeks.
Inflorescence and flower type and habit: Panicle of racemes. Individual flowers are rotate and conic.
Rate of flower opening: 2 to 4 days from bud to fully opened flower.
Flower longevity on plant: 2-10 days depending on climate.
Persistent or self-cleaning: Self-Cleaning.
Bud:
　　*Shape.*—Pyramidal.
　　*Length.*—Approx. 0.3 cm.
　　*Diameter.*—Approx. 0.2 cm.
　　*Color.*—RHS Green 141B.
Flower size:
　　*Diameter.*—Approximately 2-6 mm.
　　*Length.*—Approximately 4-10 mm.

Outer tepal:
    *Length.*—2-6 mm.
    *Width.*—3-10 mm.
    *Quantity.*—3.
    *Texture.*—Smooth.
    *Apex.*—Broadly acute.
    *Base.*—Closest to reniform.
    *Shape.*—Deltoid.
    *Margin.*—Entire.
    *Aspect.*—Concave.
Color:
    *When opening.*—Upper surface: Near RHS Yellow-Green 144A. Lower surface: Near RHS Yellow-Green 144A.
    *Fully opened.*—Upper surface: Near RHS Yellow-Green 144A. Lower surface: Near RHS Yellow-Green 144A.
    *Aging.*—Upper surface: Near RHS Yellow-Green 144A. Lower surface: Near RHS Yellow-Green 144A.
Sepals:
    *Quantity per flower.*—3.
    *Shape.*—Deltoid.
    *Length.*—2-3 mm.
    *Width.*—0.5-1.3 mm.
    *Apex.*—Obtuse.
    *Base.*—Cuneate.
    *Margin.*—Entire.
    *Texture.*—Smooth.
    *Color.*—Upper Surface: Near RHS Green 138A. Lower Surface: Near RHS Green 138A.
Peduncle:
    *Length.*—10 cm to 5 mm.
    *Diameter.*—1 mm to 5 mm.
    *Color.*—Near RHS Green 141C.
    *Orientation.*—Upright.
    *Texture.*—Glabrous.
Pedicel:
    *Length.*—Approximately 0.5-6 mm.
    *Diameter.*—Approximately 0.01-0.5 mm.
    *Color.*—Near RHS Green 141C.
    *Orientation.*—Nodding.
    *Texture.*—Smooth.
Fragrance: Not fragrant.

REPRODUCTIVE ORGANS

Stamens:
    *Number.*—6.
    *Filament length.*—Approximately 0.1-1 mm.
Anthers:
    *Shape.*—Ellipsoid with two lobes.
    *Length.*—Approximately 1-2 mm.
    *Color.*—Near RHS Green-White 157D.
Pistil:
    *Number.*—1.
    *Length.*—Approximately 0.1-1 mm.
    *Color.*—Near RHS White 155NNA.
    *Stigma.*—Shape: Cup-shaped. Color: Near RHS White NN155A. Ovary Color: Near RHS Green 141C.
Temperature tolerance: Tolerates a range from approximately 8° C. to 30° C.
Drought tolerance: Drought tolerance observed.

SEEDS/FRUIT

Fruit:
    *Type.*—Samara.
    *Length.*—Approximately 3-4 mm.
    *Width.*—Approximately 2.5-4 mm.
    *Position.*—Axillary.
    *Color.*—Near RHS Yellow-Green 144C.
    *Texture.*—Coarse.
    *Veins.*—Not veined.
Seeds:
    *Shape.*—Triquetrous.
    *Length.*—Approximately 2 mm.
    *Width.*—Approximately 1.5 mm.
Disease/pest resistance and susceptibility: Neither resistance nor susceptibility to normal diseases and pests of *Rumex* observed.

We claim:

1. A *Rumex* plant named 'DRUMFOHNID', representative biological material seed having been deposited at the NCIMB in Aberdeen, Scotland and granted Accession Number 43987.

2. A plant or a plant part thereof produced by growing the plant of claim 1, wherein the plant or plant part comprises at least one cell of *Rumex* 'DRUMFOHNID'.

3. A *Rumex* plant or part thereof, having the physiological and morphological characteristics of the plants of claim 1.

4. The tissue or cell culture of regenerable cells produced from the plant of claim 1.

5. The tissue or cell culture of claim 4, comprising tissues or cells from a plant part selected from the group consisting of leaves, vegetative cuttings, pollen, embryos, cotyledons, hypocotyl, meristematic cells, roots, root tips, pistils, anthers, flowers and stems.

6. A method of producing *Rumex* progeny comprising the steps of (a) crossing a plant of *Rumex* 'DRUMFOHNID' as a female or male parent with another *Rumex* plant and (b) selecting progeny.

7. The method according to claim 6, wherein the second plant is *Rumex* 'DRUMFOHNID'.

8. A *Rumex* seed that produces the *Rumex* plant of claim 1.

9. A method for developing a *Rumex* plant in a plant breeding program using plant breeding techniques, including crossing, recurrent selection, mutation breeding, wherein said mutation breeding selects for a mutation that is spontaneously or naturally induced or artificially induced, backcrossing, pedigree breeding, marker enhanced selection, haploid/double haploid production or transformation to a plant of *Rumex* 'DRUMFOHNID', or it's parts or progeny, wherein application of said techniques results in development of a *Rumex* plant.

\* \* \* \* \*